US009895625B2

(12) United States Patent
Lee et al.

(10) Patent No.: US 9,895,625 B2
(45) Date of Patent: *Feb. 20, 2018

(54) METHOD AND APPARATUS FOR PREPARING ISOPROPYL ALCOHOL

(71) Applicant: LG CHEM, LTD., Seoul (KR)

(72) Inventors: Sung Kyu Lee, Daejeon (KR); Jong Ku Lee, Daejeon (KR); Joon Ho Shin, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/559,632

(22) Filed: Dec. 3, 2014

(65) Prior Publication Data

US 2015/0083578 A1 Mar. 26, 2015

Related U.S. Application Data

(63) Continuation of application No. PCT/KR2013/008080, filed on Sep. 6, 2013.

(30) Foreign Application Priority Data

Sep. 6, 2012 (KR) .................. 10-2012-0098644
Sep. 6, 2013 (KR) .................. 10-2013-0107406

(51) Int. Cl.
*B01D 3/14* (2006.01)
*C07C 29/80* (2006.01)
(Continued)

(52) U.S. Cl.
CPC ............... *B01D 3/32* (2013.01); *B01D 3/007* (2013.01); *B01D 3/141* (2013.01); *C07C 29/76* (2013.01);
(Continued)

(58) Field of Classification Search
CPC ......... C07C 31/10; C07C 29/80; B01D 3/141; B01D 71/028
See application file for complete search history.

(56) References Cited

U.S. PATENT DOCUMENTS 3,122,486 A * 2/1964 Skarstrom ............ B01D 53/047
203/18
4,373,935 A * 2/1983 Ausikaitis .............. B01D 53/04
203/19
(Continued)

FOREIGN PATENT DOCUMENTS

CN 101815695 A 8/2010
CN 102060663 A 5/2011
(Continued)

OTHER PUBLICATIONS

Zeochem, "Molecular Sieves", http://www.zeochem.ch/dev/html/molecular_sieves.html.*
(Continued)

*Primary Examiner* — Jonathan Miller
*Assistant Examiner* — Jonathan Luke Pilcher
(74) *Attorney, Agent, or Firm* — Dentons US LLP (57) ABSTRACT

The present application relates to an apparatus for purifying isopropyl alcohol. The present application enables isopropyl alcohol to be obtained in a high purity from a feed comprising water and isopropyl alcohol with a minimum amount of energy consumption.

10 Claims, 4 Drawing Sheets

(51) Int. Cl.
*C07C 31/10* (2006.01)
*B01D 3/32* (2006.01)
*C07C 29/76* (2006.01)
*B01D 3/00* (2006.01)
*B01D 71/02* (2006.01)

(52) U.S. Cl.
CPC ............ *C07C 29/80* (2013.01); *B01D 71/028* (2013.01); *C07C 31/10* (2013.01)

(56) References Cited

U.S. PATENT DOCUMENTS

| | | | |
|---|---|---|---|
| 6,930,213 B1* | 8/2005 | Pompetzki | C07C 29/145 568/881 |
| 7,799,958 B2* | 9/2010 | Bonmann | C07C 37/08 568/798 |
| 9,758,458 B2* | 9/2017 | Park | C07C 29/76 |
| 2009/0093656 A1* | 4/2009 | Bonmann | C07C 37/08 568/798 |
| 2016/0200649 A1* | 7/2016 | Park | B01D 15/08 568/916 |
| 2016/0200650 A1* | 7/2016 | Park | B01D 61/362 568/913 |

FOREIGN PATENT DOCUMENTS

| | | |
|---|---|---|
| CN | 102452897 A | 5/2012 |
| EP | 0272146 | 6/1988 |
| JP | 10109948 | 4/1998 |
| JP | 11035504 | 2/1999 |
| JP | 11-276801 A | 10/1999 |
| JP | 2010-540582 A | 12/2010 |
| KR | 10-2004-0085710 A | 10/2004 |
| KR | 100790413 | 1/2008 |

OTHER PUBLICATIONS

English Translation of Nobuyuki et al., JP 11(1999)-276801) A, Oct. 12, 1999, Translation obtained from APIN.*
Shah, P.B., "Squeeze More Out of Complex Columns," CEP Magazine, Jul. 2002, pp. 46-55.

* cited by examiner

METHOD AND APPARATUS FOR PREPARING ISOPROPYL ALCOHOL

CROSS-REFERENCE TO RELATED APPLICATIONS

This application is a Continuation Bypass Application of International Patent Application No. PCT/KR2013/008080, filed Sep. 6, 2013, and claims the benefit of Korean Application No. 10-2012-0098644, filed Sep. 6, 2012 and Korean Application No. 10-2013-0107406, filed on Sep. 6, 2013, all of which are hereby incorporated herein by reference in their entirety for all purposes as if fully set forth herein.

BACKGROUND OF THE INVENTION

Field of the Invention

The present application relates to a method and an apparatus for preparing isopropyl alcohol.

Description of Related Art

Isopropyl alcohol (hereinafter referred to as IPA) is used for various uses, for example, including use as a cleaning agent in electronics industries such as the semiconductor and liquid crystal display (LCD) manufacturing industries.

IPA may be prepared, for example, by using propylene or acetone as a raw material. In most cases, a reactant including IPA is an azeotrope also including water. That is, water, which has a boiling point of about 100° C., and IPA, which has a boiling point of about 82.3° C., form an azeotrope at an azeotropic temperature of about 79.5° C., which makes it very difficult to remove the water from the feed.

BRIEF SUMMARY OF THE INVENTION

The present application provides a method and an apparatus for preparing IPA.

Figure 1:
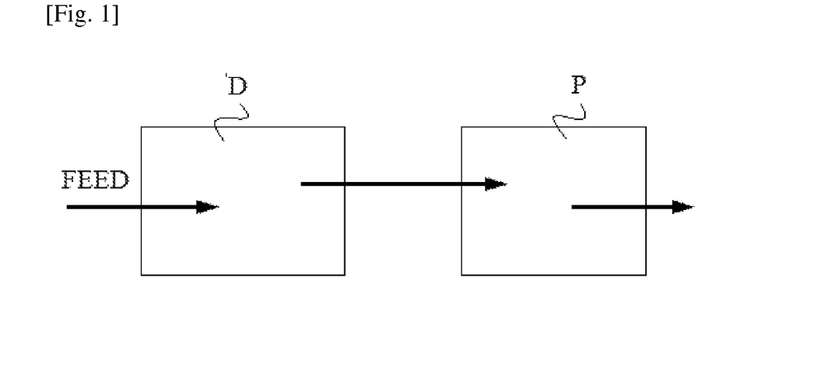
FIG. 1 is a diagram illustrating a process of the method described above.

The present application relates to a method for preparing IPA. An exemplary preparing method may include a process 100 of supplying a feed to a dehydration means and removing water (hereinafter also referred to as a dehydration process D), and a purifying process 200 (hereinafter also referred to as a purification process P) by introducing the feed from which the water is removed via the dehydration means into a purification means, such as a divided wall column (DWC) as shown in FIG. 1.

In one example, the feed supplied to the dehydration means may include IPA and water. The water content of the feed, that is, the content of water within the feed, may be 10,000 ppm or less, 2,500 ppm or less, or 2,200 ppm or less. In addition, the lower limit of the water content within the feed may be 1,000 ppm. The water content within the feed acts as a very important factor on the efficiency of the method mentioned above, and thus needs to be adjusted within the range described above. A specific composition of the feed is not particularly limited as long as the feed includes IPA and water and the water content is adjusted to be within these ranges. Typically, various kinds of impurities may be included within the feed depending on how the feed including IPA is prepared, and the impurities may be effectively removed by the method described above.

The dehydration means into which the feed is to be introduced in the method may include, for example, molecular sieves (MS). When the feed having the water content of 3,000 ppm is introduced, the dehydration means including the MS, for example, may be installed to decrease the water content percentage within the feed to 300 ppm or less, 250 ppm or less, 200 ppm or less, 150 ppm or less, or 100 ppm or less and then discharge the feed through the dehydration process D. Accordingly, the method may include removing the water from the feed supplied to the dehydration means and adjusting the percentage of water content of the feed to 300 ppm or less, 250 ppm or less, 200 ppm or less, 150 ppm or less, or 100 ppm or less. By adjusting the percentage of water content with the dehydration means to the range mentioned above, the efficiency of the subsequent purification process P may be enhanced.

As the molecular sieve of the dehydration means, a well-known molecular sieve may be used without particular limitation as long as the molecular sieve having the dehydration ability as described above is provided. For example, as the molecular sieve, a zeolite-based molecular sieve, a silica-base molecular sieve, an alumina-based molecular sieve, and so forth, are may be used.

As, the molecular sieve, the molecular sieve having an average pore size of about 1.0 Å to 5.0 Å or about 2.0 Å to 3.0 Å is may be used. In addition, the specific surface area of the molecular sieve may be, for example, about 10 m³/g to 3,000 m³/g. By using the molecular sieve with the pore size and the specific surface area mentioned above, it is possible to properly adjust the dehydration ability of the dehydration means.

Figure 2:
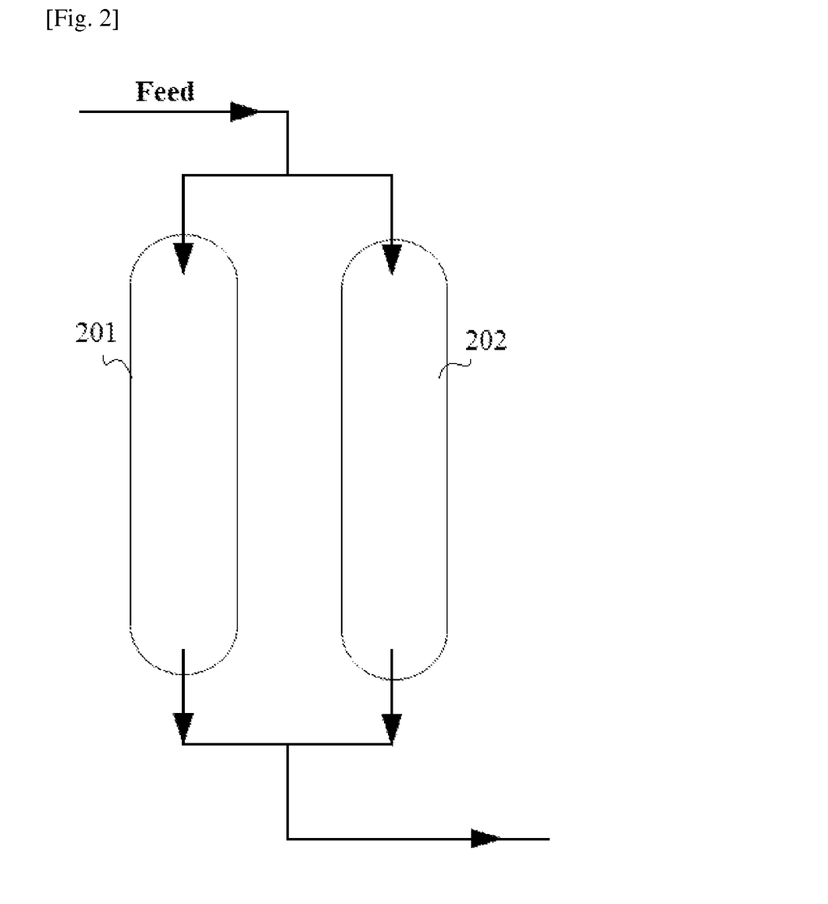
FIG. 2 is a diagram illustrating a dehydration means used in the method.

In one example, the dehydration means may include a column with which the molecular sieves are filled. The dehydration means may include, for example, at least two or more of the column described above. FIG. 2 illustrates an exemplary case in which the dehydration means includes two columns 201 and 202 filled with the molecular sieves. When two or more columns are included in the dehydration means and the feed is alternately supplied to the columns as shown in FIG. 2, the efficiency of the process may be enhanced.

Introducing the feed into the molecular sieve in the dehydration process D may be carried out, for example, at a temperature of about 20° C. to 135° C. or about 30° C. to 80° C. In addition, introducing the feed into the molecular sieve may be carried out, for example, at a pressure of 1.0 Kg/cm² to 10.0 Kg/cm² or 4.0 Kg/cm² to 6.0 Kg/cm². The dehydration process D may be effectively carried out at the temperature and the pressured described above. However, the range of the temperature and/or the pressure may be properly changed depending on the kind of the MS to be used and the desired amount of dehydration.

The method may further include regenerating the molecular sieve by desorbing the water adsorbed onto the molecular sieve in the dehydration process D. The desorbing process for the molecular sieve, for example, may be carried out during the purification process P subsequent to the dehydration process D, or may be carried out on any one column while the dehydration process D of another column is in progress when the plurality of columns are used as described above.

The regeneration may be carried out, for example, using hydrogen or nitrogen gas, or lower alkanes such as methane, ethane, propane, or butane. For example, the regeneration process may be carried out using nitrogen gas. In a case of using nitrogen gas, the regeneration process may be carried out at a temperature of about 180° C. to 300° C. or 200° C. to 260° C. In addition, the flow rate of the nitrogen gas supplied for desorption may be adjusted, for example, to about 7 tons/hr to 18 tons/hr. The regeneration process and the desorption process may be effectively carried out within the range described above. However, the temperature and the flow rate may be changed depending on the usage or kind of the specific molecular sieve.

The feed of which the water content is adjusted to 300 ppm or less through the dehydration process D may be supplied to the purification means, and the purification process P may be carried out. The purification means for carrying out the purification process P may include, for example, one or more distillation columns.

In one example, the purification process P may be carried out in the Divided Wall Column (DWC). The divided wall column is a device designed to distill the feed including three components having low, middle, and high boiling points, respectively. The divided wall column is a device similar to a so-called Petlyuk column in a view of thermodynamics. In the case of a Petlyuk column, a prefractionator and a main distillation column are disposed in a thermally integrated structure, the low- and high-boiling point components are primarily separated from each other in the prefractionator, a top and bottom of the prefractionator are introduced into respective supplying plates of the main distillation column, and the low-, middle-, and high-boiling point components are separated from each other in the main distillation column. On the other hand, the divided wall column has a structure in which a divided wall is disposed within the column to incorporate the prefractionator into the main distillation column.

Figure 3:
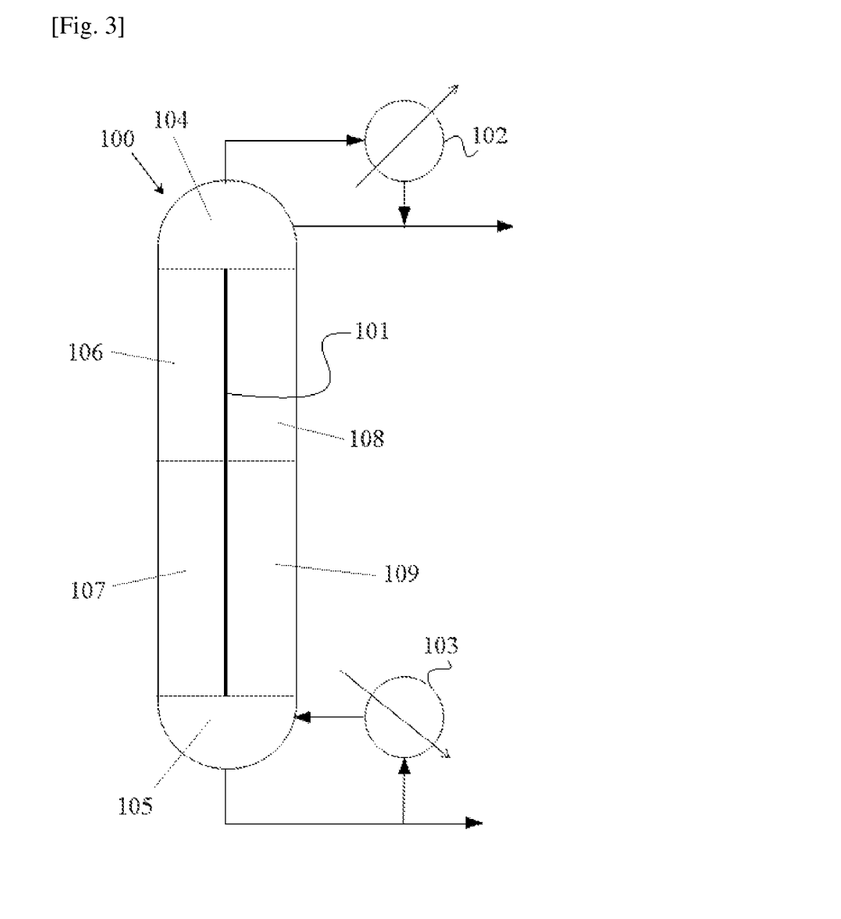
FIGS. 3 to 5 are diagrams illustrating a purification means used in the method.

For example, the divided wall column may have a structure as shown in FIG. 3. FIG. 3 illustrates an exemplary divided wall column 100. As shown in FIG. 3, the exemplary divided wall column 100 may have a structure in which the inside is divided by the divided wall 101 and a condenser 102 of an upper portion and a reboiler 103 of a lower portion are included. In addition, as shown in FIG. 3, the inside of the divided wall column 100 may be virtually divided along dotted lines so that the inside may be divided into a top region 104, a bottom region 105, an upper supply region 106, a lower supply region 107, an upper discharge region 108, and a lower discharge region 109. In particular, the ⌜upper and lower supply regions⌟ may be upper and lower regions bisected in a longitudinal direction of the divided wall column 100 in a space into which the feed is to be supplied and divided by the divided wall 101 in the structure of the divided wall column, respectively. In addition, the ⌜upper and lower discharge regions⌟ may be upper and lower discharge regions bisected in a longitudinal direction of the divided wall column 100 in a space into which a product feed is to be discharged and divided by the divided wall 101 in the structure of the divided wall column, respectively.

A specific kind of the divided wall column that may be employed in the purification process P is not particularly limited. For example, the divided wall column having a general structure as shown in FIG. 3 may be employed, or the divided wall column in which the position or shape of the divided wall is changed in consideration of the purification efficiency may be employed.

For example, the divided wall column may be installed to supply the feed passed through the dehydration means into the upper supply region of the divided wall column. Accordingly, the feed passed through the dehydration process D may be supplied into the upper supply region of the divided wall column in the purification process P. For example, at the time of supplying the feed into the divided wall column, purification may be effectively carried out in consideration of the composition of the feed when the feed is supplied into the upper supply region 106 as shown in FIG. 3.

The feed may be supplied into the divided wall column, for example, at a flow rate of about 5,000 Kg/hr to 13,000 Kg/hr. In addition, the temperature at which the feed is supplied may be adjusted to, for example, about 75° C. to 135° C., about 80° C. to 100° C., or about 85° C. to 95° C. When the feed is supplied at the flow rate and the temperature described above, proper distillation efficiency may be obtained.

The driving temperature of the upper portion of the divided wall column may be adjusted to, for example, about 40° C. to 140° C. or about 45° C. to 80° C. when the distillation is carried out after the feed is supplied into the divided wall column. In addition, the driving temperature of a lower portion of the divided wall column may be adjusted to, for example, about 90° C. to 170° C. or about 100° C. to 116° C. When the driving conditions of the divided wall column are adjusted as described above, the distillation depending on the feed composition may be effectively carried out.

The driving conditions of the divided wall column may be additionally adjusted if necessary in consideration of the purification efficiency or the like.

For example, the driving pressure of the upper portion of the divided wall column in the purification process P may be adjusted to about 0.1 Kg/cm$^2$ to 10.0 Kg/cm$^2$, or 0.2 Kg/cm$^2$ to 1.2 Kg/cm$^2$. At this driving pressure, the distillation depending on the feed composition may be effectively carried out. The divided wall column may be installed to discharge the product including the IPA from the lower discharge region after being subjected to the procedure described above. That is, the preparation method described above may include obtaining the product including the IPA from the lower discharger region of the divided wall column. As described above, the efficiency of the purification process P may be further increased by adjusting the discharge position of the product.

Figure 4:
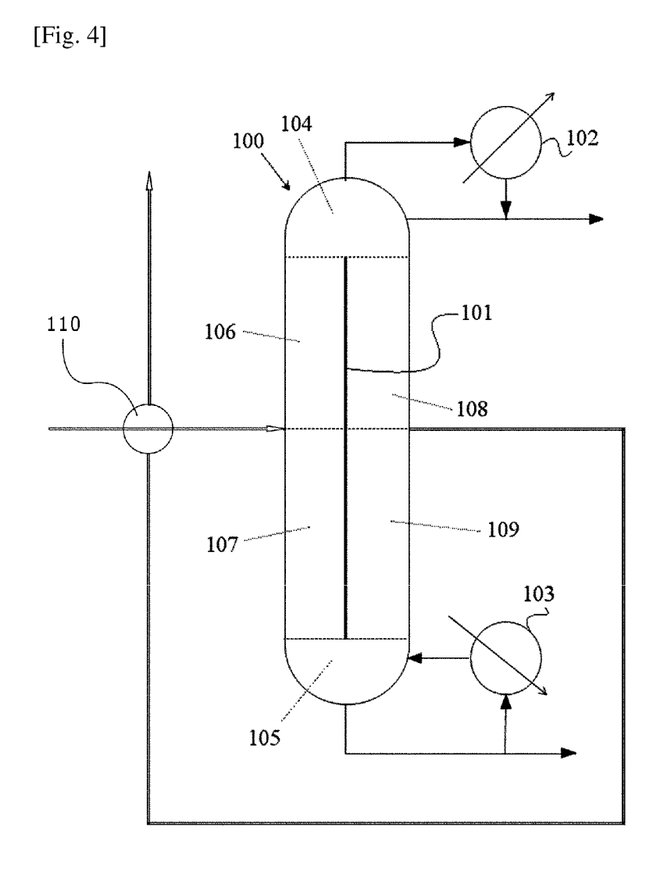

For example, as shown in FIG. 4, heat may be exchanged between the flow of the product including the IPA discharged from the lower discharge region of the divided wall column and feed introduced into the divided wall column through a heat exchanger 110. When heat is exchanged between the product flow and the feed as described above, the reflux ratio of the flow discharged from the bottom region of the divided wall column may be 1,000 to 3,000, and the purification efficiency may be maximized by adjusting the reflux ratio of the bottom region within the range.

The energy consumption necessary to preheat the feed may be reduced by exchanging heat between the flow of the product discharged from the lower discharge region of the divided wall column and the feed introduced into feed supply region of the divided wall column. In addition, the effect of saving cost consumed in the condensation process may be additionally obtained by reducing an amount of cooling water used in the condensation process using the condenser before the flow including IPA is condensed and produced as a product.

In another implementation, the purification process P may be carried out in at least two columns, for example, two distillation columns. In this case, the feed passed through the dehydration means may be introduced into the first distillation column and purified, and the lower discharge of the first distillation column may be introduced into the second distillation column again and purified. In this case, the IPA may be discharged, for example, from the upper region of the second distillation column.

Figure 5:
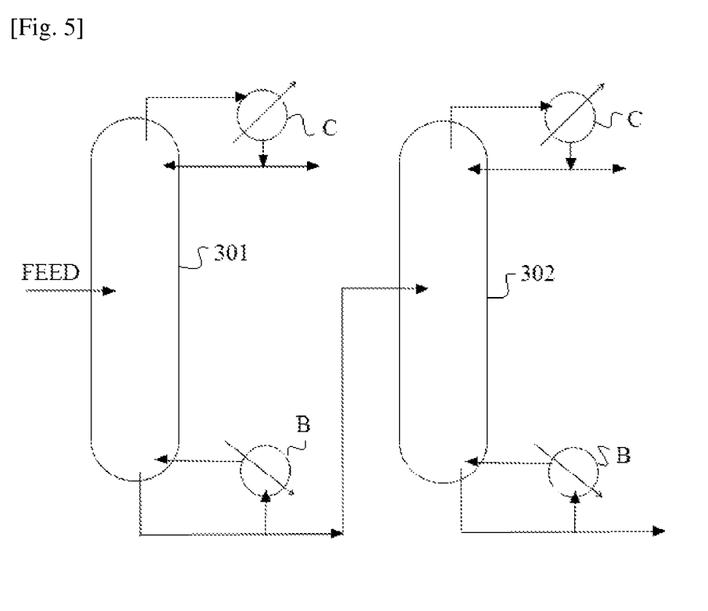

FIG. 5 illustrates the purification means including two distillation columns, that is, the first distillation column 301 and the second distillation column 302, as an exemplary purification means. Each of the distillation columns 301 and 302 includes a condenser C and a reboiler B.

When the purification means as shown in FIG. 5 is employed, the feed passed through the dehydration means is first supplied into the first distillation column 301 and purified. During this process, for example, a driving temperature of the upper portion of the first distillation column may be adjusted to about 40° C. to 66° C. or about 45° C. to 60° C. In addition, a driving temperature of a lower portion of the first distillation column may be adjusted to about 80° C. to 135° C. or about 85° C. to 130° C. In addition, for example, a driving pressure of the upper portion of the first distillation column may be adjusted to about 0.1 Kg/cm$^2$ to 10.0 Kg/cm$^2$ or about 0.2 Kg/cm$^2$ to 1.2 Kg/cm$^2$. Under these conditions, the purification process P in the first distillation column may be effectively carried out. By means of the process described above, the low-boiling component within the feed may be discharged from the upper portion of the first distillation column and the remaining discharge of the lower portion may be supplied into the second distillation column.

In the second distillation column 302, the feed supplied from the first distillation column may be purified.

During this process, for example, a driving temperature of the upper portion of the second distillation column may be adjusted to about 40° C. to 130° C. or about 60° C. to 80° C. In addition, a driving temperature of the lower portion of the second distillation column may be adjusted to about 90° C. to 170° C. or about 100° C. to 120° C. In addition, for example, a driving pressure of the upper portion of the second distillation column may be adjusted to about 0.1 Kg/cm$^2$ to 10.0 Kg/cm$^2$ or about 0.2 Kg/cm$^2$ to 1.2 Kg/cm$^2$. Under these conditions, the purification process P in the second distillation column may be effectively carried out. By means of the process described above, the product including IPA may be discharged from the upper portion of the second distillation column.

Other conditions of the distillation column or the divided wall column in which the purification process P is carried out, for example, the number of plates or the inner diameter of each distillation column, or the reflux rate of the discharge of the upper portion or the lower portion, are not particularly limited. For example, the number of theoretical plates of each distillation column may be determined on the basis of the number of theoretical plates calculated by the distillation curve of the feed or the like. In addition, for example, the flow rate or the reflux ratio of the discharges of the upper and lower portion in each distillation column may be set to allow the driving pressure and temperature described above to be obtained.

The present application also relates to an apparatus for preparing IPA. An exemplary preparation apparatus may be an apparatus to be applied to the preparation method described above.

Accordingly, the preparation apparatus may include the dehydration means installed to decrease the water content of the feed to 300 ppm or less and then discharge the water content, and the divided wall column into which the feed passed through the dehydration means is introduced and the purification process P is carried out when the feed is supplied as described above.

For example, particulars described above may be applied to details associated with the preparation apparatus.

For example, the dehydration means may include the molecular sieve such as the zeolite-based molecular sieve, the silica-based molecular sieve, or the alumina-based molecular sieve. As the molecular sieve, the molecular sieve having the average pore size and the specific surface area as described above is may be used.

The dehydration means may include, for example, two or more columns in which the MS s are filled.

The preparation apparatus may further include, for example, a regeneration means including a desorbing agent such as nitrogen gas, as a means capable of regenerating the molecular sieve of the dehydration means. In addition, the preparation apparatus may further include a heating means, for example, a heat exchanger into which steam or the like is supplied, being capable of heating the nitrogen gas to a predetermined temperature and supplying the gas during the desorbing and regeneration process.

The divided wall column of the preparation apparatus acts as the purification means for carrying out the purification process P on the feed of which the water content is adjusted to 300 ppm or less through the dehydration process D, and the divided wall column may be installed to supply the feed subjected to the dehydration into the upper supply region of the divided wall column. In addition, the divided wall column may be installed to discharge the product including the IPA from the lower discharge region.

In another implementation, the purification process P may be carried out using the two or more distillation columns described above instead of the divided wall column mentioned above.

According to the present application, it is possible to obtain IPA in a high purity from a feed including water and IPA with a minimum amount of energy consumption.

DETAILED DESCRIPTION OF THE INVENTION

Best Mode of Carrying Out the Invention

Hereinafter, the method will be described in detail in terms of examples and comparative examples. However, the method and the apparatus are not limited to the examples described below.

Example 1

Processes were carried out using a dehydration means which has two columns disposed as shown in FIG. 2, and a the divided wall column connected to the dehydration means as shown in FIG. 3 as a purification means. In this case, the two columns having a volume of about 8 m$^3$ were filled with about 5,880 Kg of a zeolite 3A which has an average pore size of about 2 Å to 3 Å and a specific surface area of about 15 m$^3$/g, serving as an molecular sieve. Regeneration of the molecular sieve was carried out using a means capable of supplying nitrogen gas at a flow rate of about 8 tons/hr at about 230° C. A feed including IPA at 98.6% by weight, water at about 3,000 ppm, and other impurities at about 1.1% by weight was employed. The feed was supplied to the dehydration means, and the dehydration process was carried out so that the water content within the feed was about 300 ppm or less. The feed of which the water content was adjusted to 300 ppm or less through the dehydration process D was then supplied to the upper supply region 106 of the divided wall column 100 and purification was carried out, and the product including IPA was obtained in the lower discharge region 109. In addition, the driving temperature and the pressure of the upper portion of the divided wall column 100 were adjusted to about 58° C. and 1.2 Kg/cm², and the driving temperature of the lower portion of the divided wall column was adjusted to about 108° C.

Example 2

The processes were carried out in the same way as in the Example 1 except that heat was exchanged between the flow of the product including IPA obtained in the lower discharge region 109 of the divided wall column and the feed by means of the heat exchanger.

Comparative Example 1

The processes were carried out in the same way as in the Example 1 except that the water content within the feed introduced into the purification means through the dehydration means was adjusted to about 400 ppm.

Comparative Example 2

The processes were carried out in the same way as in the Example 1 except that the feed was directly introduced into the divided wall column as shown in FIG. 3 without being subjected to the dehydration process D. The driving temperature and pressure of the upper portion of the divided wall column were adjusted to about 145° C. to 155° C. and 10 to 12 Kg/cm², and the driving temperature of the lower portion was adjusted to about 175° C. to 185° C. The number of theoretical plates and the inner diameter of the divided wall column were determined on the basis of the number of theoretical plates obtained in the distillation curve.

Heat duties for the reboiler, the condenser and the heating means for the desorbing gas in the each processes, and additional recovery amounts of IPA in Examples 1 and 2 compared to the Comparative Example 2 are summarized in table 1 below.

|  |  | Example 1 | Example 2 | Comparative Example 1 | Comparative Example 2 |
|---|---|---|---|---|---|
| HEAT DUTY (Gcal/hr) | Condenser | 1.58 | 1.30 | 1.80 | 2.82 |
|  | Reboiler | 1.57 | 1.29 | 1.79 | 2.82 |
|  | Heating means for regenerating adsorbing agent | 0.20 | 0.20 | 0.20 | 0.00 |
| Amount of saved energy (Gcal/hr) |  | 1.77 | 1.49 | 1.99 | — |
| Saved energy rate (%) |  | 37 | 47 | 29 | — |
| Additional recovery amount of IPA (Kg/hr) |  | 110~115 | 110~115 | 100~105 | 110~115 |

Amount of saved energy: amount of saved energy compared to second comparative example
Saved energy rate: saved energy rate compared to second comparative example
Additional recovery amount of IPA: additional recovery amount compared to second comparative example

The invention claimed is:

1. A method for preparing isopropyl alcohol, comprising:
supplying a feed including isopropyl alcohol and water and having a water content of 1,000 ppm to 10,000 ppm to a dehydration column including molecular sieves;
removing the water with the dehydration column to adjust the water content of the feed to 300 ppm or less; and
supplying the feed of which the water content is adjusted to 300 ppm or less to a divided wall column to carry out purification,
wherein the divided wall column comprises a top region, a supply region, a discharge region, a bottom region and a dividing wall, wherein the dividing wall divides the divided wall column between the top region and the bottom region into the supply region and the discharge region,
wherein the supply region is bisected along a longitudinal direction of the divided wall column to form an upper supply region and a lower supply region, and the discharge region is bisected along a longitudinal direction of the divided wall column to form an upper discharge region and a lower discharge region,
wherein the purification includes supplying the feed of which the water content is adjusted to 300 ppm or less into the upper supply region of the divided wall column, carrying out purification in the divided wall column, and obtaining a discharge including the purified isopropyl alcohol from the lower discharge region of the divided wall column,
wherein upper and lower driving temperatures of the divided wall column are adjusted to 40° C. to 140° C. and 90° C. to 170° C., respectively,
wherein a driving pressure of the upper portion of the divided wall column is adjusted to 0.1 Kg/cm² to 10.0 Kg/cm²,
wherein heat is exchanged between the discharge from the lower discharge region of the divided wall column and the feed supplied to the upper supply region of the divided wall column, and
wherein a reflux ratio of the discharge from the lower discharge region of the divided wall column is 1,000 to 3,000.

2. The method of claim 1, wherein an average pore size of the molecular sieves is 1.0 Å to 5.0 Å.

3. The method of claim 1, wherein the molecular sieves have a specific surface area of 10 m²/g to 3,000 m²/g.

4. The method of claim 1, wherein the dehydration column includes a column in which the molecular sieves are filled.

5. The method of claim 1, further comprising:
using nitrogen gas to regenerate the molecular sieves that have been used to adjust the water content of the feed.

6. The method of claim 5, wherein the regeneration is carried out at 180° C. to 300° C.

7. An apparatus for preparing isopropyl alcohol, comprising:
a dehydration column including molecular sieves and installed to adjust a water content of a feed to 300 ppm or less and to discharge the feed when the feed including isopropyl alcohol and water and having the water content of 1,000 ppm to 10,000 ppm is supplied to the dehydration column;
a divided wall column installed to allow the feed passed through the dehydration column to be introduced and purification process to be carried out, wherein the divided wall column comprises a top region, a supply region, a discharge region, a bottom region and a divided wall, the divided wall dividing the divided wall column between the top region and the bottom region into the supply region and the discharge region, the supply region being bisected along a longitudinal direction of the divided wall column to form an upper supply region and a lower supply region, and the discharge region being bisected along a longitudinal direction of the divided wall column to form an upper discharge region and a lower discharge region; and a heat exchanger installed to exchange heat between a discharge from the lower discharge region of the divided wall column and the feed supplied into the upper supply region of the divided wall column, wherein the divided wall column is installed to supply the feed of which the water content is adjusted to 300 ppm or less into the upper supply region and to discharge the purified isopropyl alcohol from the supplied feed to the lower discharge region, wherein upper and lower driving temperatures of the divided wall column are 40° C. to 140° C. and 90° C. to 170° C., respectively, wherein driving pressure of the upper portion of the divided wall column is 0.1 $Kg/cm^2$ to 10.0 $Kg/cm^2$, and wherein a reflux ratio of the discharge from the lower discharge region of the divided wall column is 1,000 to 3,000.

8. The apparatus of claim 7, wherein an average pore size of the molecular sieves is 1.0 Å to 5.0 Å.

9. The apparatus of claim 7, wherein the molecular sieves have a specific surface area of 10 $m^2/g$ to 3,000 $m^2/g$.

10. The apparatus of claim 7, further comprising:

a regenerator including a nitrogen gas as a desorbing agent for the molecular sieves.

* * * * *